United States Patent
Williams et al.

(10) Patent No.: US 10,952,729 B2
(45) Date of Patent: Mar. 23, 2021

(54) UNIVERSAL LINEAR BUTTRESS RETENTION/RELEASE ASSEMBLIES AND METHODS

(71) Applicant: Covidien LP, Mansfield, MA (US)

(72) Inventors: Justin Williams, Southbury, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 16/150,301

(22) Filed: Oct. 3, 2018

(65) Prior Publication Data

US 2020/0107830 A1  Apr. 9, 2020

(51) Int. Cl.
*A61B 17/072* (2006.01)
*A61B 17/00* (2006.01)

(52) U.S. Cl.
CPC ............ *A61B 17/07292* (2013.01); *A61B 2017/00884* (2013.01); *A61B 2017/07271* (2013.01)

(58) Field of Classification Search
CPC .... A61B 17/07292; A61B 2017/00884; A61B 2017/07271
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Extended European Search Report corresponding to EP 14 16 9739.1, completed Aug. 19, 2014 and Aug. 29, 2014; (7 pp).

(Continued)

*Primary Examiner* — Nathaniel C Chukwurah
*Assistant Examiner* — Lucas E. A. Palmer
(74) *Attorney, Agent, or Firm* — Carter DeLuca & Farrell LLP

(57) ABSTRACT

A surgical stapling apparatus includes a buttress retention assembly. The buttress retention assembly includes a sleeve configured to be detachably coupled with a first jaw member of a tool assembly of the surgical stapling apparatus, and a buttress material. The sleeve includes a proximal hook extending transversely outward from a lateral side of the sleeve, and a mouth including a hook configured to be received in a knife slot of the first jaw member. The mouth includes an inner surface having an inwardly extending boss. The buttress material includes a tab extending transversely outward from a lateral side thereof. The tab defines a proximal slot configured to receive the proximal hook of the sleeve. At least a portion of the distal end portion extends through the mouth of the sleeve. The distal end portion defines a distal slot dimensioned to receive the boss of the sleeve.

17 Claims, 11 Drawing Sheets

(56) References Cited

U.S. PATENT DOCUMENTS

| | | |
|---|---|---|
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,476,206 A * | 12/1995 | Green ............. A61B 17/07207 227/176.1 |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A * | 8/1996 | McKean ........... A61B 17/07207 227/178.1 |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A * | 9/1998 | Rayburn ........... A61B 17/07207 227/176.1 |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A * | 5/1999 | Frater ............... A61B 17/07207 606/148 |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A * | 8/2000 | Gabbay ............. A61B 17/07207 227/176.1 |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 * | 10/2003 | Gabbay ................ A61B 17/072 606/139 |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |

(56) References Cited

U.S. PATENT DOCUMENTS

| | | | |
|---|---|---|---|
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,207,471 B2 * | 4/2007 | Heinrich ............... A61B 17/072 227/175.1 |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 * | 5/2008 | Zubik ................... A61B 17/072 606/151 |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 * | 7/2009 | de la Torre ...... A61B 17/07207 227/176.1 |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 * | 2/2010 | Prommersberger ... A61B 17/32 227/175.1 |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |

(56) References Cited

U.S. PATENT DOCUMENTS

| | | |
|---|---|---|
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,657,176 B2 * | 2/2014 | Shelton, IV ............ A61B 17/29 227/178.1 |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,539 B2 | 4/2015 | Kostrzewski et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,662 B2 * | 12/2015 | Barton ................ A61B 17/068 |
| 9,198,663 B1 | 12/2015 | Marczyk et al. |
| 9,204,881 B2 | 12/2015 | Penna |
| 9,211,120 B2 * | 12/2015 | Scheib ............. A61B 17/07207 |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,984 B2 * | 7/2016 | Aronhalt ........ A61B 17/07292 |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek et al. |
| 10,588,623 B2 * | 3/2020 | Schmid ............ A61B 17/07292 |
| 2002/0091397 A1 | 7/2002 | Chen |
| 2002/0151911 A1 | 10/2002 | Gabbay |
| 2002/0165559 A1 * | 11/2002 | Grant ................ A61B 17/07207 606/139 |
| 2002/0165562 A1 * | 11/2002 | Grant ................ A61B 17/07207 606/151 |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |

(56) References Cited

U.S. PATENT DOCUMENTS

| | | |
|---|---|---|
| 2006/0025816 A1* | 2/2006 | Shelton, IV ..... A61B 17/07207 606/215 |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0118163 A1* | 5/2007 | Boudreaux .......... A61B 17/064 606/157 |
| 2007/0203510 A1 | 8/2007 | Bettuchi |
| 2007/0243227 A1 | 10/2007 | Gertner |
| 2007/0246505 A1* | 10/2007 | Pace-Floridia ....... A61L 31/044 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1* | 11/2008 | Bettuchi .............. A61B 17/068 227/176.1 |
| 2008/0314960 A1* | 12/2008 | Marczyk .............. A61B 17/105 227/178.1 |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0134200 A1* | 5/2009 | Tarinelli ........... A61B 17/07207 227/180.1 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1* | 9/2009 | Aranyi ............. A61B 17/07292 227/176.1 |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1* | 6/2010 | Olson .................. A61B 17/105 227/175.1 |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0074199 A1* | 3/2012 | Olson .............. A61B 17/07292 227/177.1 |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0241499 A1* | 9/2012 | Baxter, III ......... A61B 17/0643 227/176.1 |
| 2012/0253298 A1 | 10/2012 | Henderson et al. |
| 2013/0062391 A1* | 3/2013 | Boudreaux ...... A61B 17/07207 227/175.1 |
| 2013/0146641 A1* | 6/2013 | Shelton, IV ......... A61B 17/105 227/176.1 |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1* | 2/2014 | Merchant ......... A61B 17/07292 227/176.1 |
| 2014/0131418 A1 | 5/2014 | Kostrzewski |
| 2014/0239047 A1 | 8/2014 | Hodgkinson et al. |
| 2014/0263550 A1 | 9/2014 | Aranyi |
| 2015/0041347 A1 | 2/2015 | Hodgkinson |
| 2015/0119932 A1* | 4/2015 | Knodel ............ A61B 17/07292 606/219 |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0282809 A1* | 10/2015 | Shelton, IV ......... A61B 17/105 227/176.1 |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0056016 A1* | 3/2017 | Barton ............. A61B 17/07292 |
| 2017/0086836 A1* | 3/2017 | Harris .................. A61L 17/105 |
| 2017/0150967 A1 | 6/2017 | Hodgkinson et al. |
| 2017/0172575 A1* | 6/2017 | Hodgkinson .... A61B 17/07207 |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1* | 10/2017 | Ingmanson .......... A61B 17/068 |
| 2017/0354415 A1* | 12/2017 | Casasanta, Jr. ...... A61B 17/068 |
| 2018/0125491 A1* | 5/2018 | Aranyi ............. A61B 17/07207 |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1* | 8/2018 | Racenet ................ A61N 5/1007 |
| 2018/0250000 A1* | 9/2018 | Hodgkinson .... A61B 17/07207 |
| 2018/0256164 A1* | 9/2018 | Aranyi ................. A61B 17/072 |
| 2019/0059896 A1* | 2/2019 | Beardsley ........ A61B 17/07207 |
| 2019/0090871 A1* | 3/2019 | Shelton, IV ..... A61B 17/07207 |
| 2019/0254671 A1* | 8/2019 | Shankarsetty ... A61B 17/07292 |
| 2019/0343522 A1* | 11/2019 | Williams ............ A61B 17/1155 |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 1621141 A2 | 2/2006 |
| EP | 2198787 A1 | 6/2010 |
| EP | 2491867 A1 | 8/2012 |
| EP | 3135215 A1 | 3/2017 |
| EP | 3257450 A1 | 12/2017 |
| EP | 3363383 A1 | 8/2018 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 9926826 A2 | 6/1996 |
| WO | 98/38923 A1 | 9/1998 |
| WO | 0010456 A1 | 3/2000 |
| WO | 0016684 A1 | 3/2000 |
| WO | 2008109125 A1 | 9/2008 |
| WO | 2010/075298 A2 | 7/2010 |

OTHER PUBLICATIONS

Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).

(56) References Cited

OTHER PUBLICATIONS

Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.

(56) References Cited

OTHER PUBLICATIONS

Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (6 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).

(56) References Cited

OTHER PUBLICATIONS

Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 4, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Partial European Search Report issued in European Patent Application No. 19200984.3, dated Feb. 4, 2020.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report issued in European Patent Application No. 19200984.3, dated May 14, 2020.

\* cited by examiner

UNIVERSAL LINEAR BUTTRESS RETENTION/RELEASE ASSEMBLIES AND METHODS

BACKGROUND

Technical Field

The present disclosure relates to retention assemblies for staple line buttress materials, and more particularly, to assemblies and methods for detachably securing or retaining staple line buttress materials to a surgical stapling apparatus.

Background of Related Art

Surgical stapling apparatus are employed by surgeons to sequentially or simultaneously apply one or more rows of fasteners, e.g., staples or two-part fasteners, to body tissue for the purpose of joining segments of body tissue together. When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible reinforcing material or "buttress" material, between the staple and the underlying tissue. In this method, a layer of buttress material is placed against the tissue and the tissue is stapled in the conventional manner.

Accordingly, new systems and methods that are reliable and that enable easy and efficient attachment and removal of a buttress material to the surgical stapling apparatus would be desirable.

SUMMARY

The present disclosure describes attachment structures for securing a buttress material to a surgical stapling apparatus that demonstrate a practical approach to meeting the performance requirements and overcoming the usability challenges associated with buttress material attachment and removal. In general, the present disclosure describes a surgical stapling apparatus that includes a handle assembly, an elongate member extending from the handle assembly, and an end effector operatively coupled with the handle assembly.

In accordance with an embodiment of the present disclosure, there is provided a surgical stapling apparatus. The surgical stapling apparatus includes a handle including an actuation trigger, a tool assembly operatively coupled to the handle, and a buttress retention assembly. The tool assembly includes a first jaw member and a second jaw member. The buttress retention assembly includes a sleeve configured to be detachably coupled with the first jaw member, and a buttress material including a proximal end portion and a distal end portion. The sleeve includes proximal and distal portions. The proximal portion of the sleeve includes a proximal hook extending transversely outward from at least one lateral side of the proximal portion of the sleeve. The distal portion of the sleeve includes a mouth defining an aperture. The mouth includes a hook configured to be at least partially received in a knife slot of the first jaw member. The mouth includes an inner surface having an inwardly extending boss. The buttress material includes a tab extending transversely outward from a lateral side of the proximal end portion of the buttress material. The tab defines a proximal slot configured to receive the proximal hook of the sleeve. At least a portion of the distal end portion of the buttress material extends through the aperture of the mouth of the sleeve. The distal end portion of the buttress material defines a distal slot dimensioned to receive the boss of the sleeve.

In an embodiment, the buttress material may be formed of an elastic material such that when the buttress material is supported on the sleeve, cutting of the buttress material along a length thereof by a knife of the tool assembly causes the hook of the mouth to urge the buttress material inward towards the knife slot of the first jaw member, whereby the boss of the sleeve is released from the distal slot of the buttress material.

In another embodiment, the proximal end portion of the buttress material may define a slit dimensioned to receive a knife of the tool assembly.

In yet another embodiment, the sleeve may include an arcuate shape configured to receive the first jaw member.

In still yet another embodiment, the proximal portion of the sleeve may include a plurality of lips extending transversely outward from opposing lateral sides thereof to engage the first jaw member.

In an embodiment, the proximal portion of the sleeve may include a plurality of proximal hooks disposed on the opposing lateral sides of the proximal portion of the sleeve.

In another embodiment, each proximal hook may be interposed between adjacent lips.

In an embodiment, the sleeve may be secured with the first jaw member by snap-fit or interference fit configuration.

In yet another embodiment, the mouth of the sleeve may include a nose having sides configured to displace the hook of the sleeve away from the anvil when the sides of the nose are squeezed together.

In yet another embodiment, the mouth may include an inner surface defining an acute angle with respect to a longitudinal axis defined by the anvil.

In still yet another embodiment, the boss may extend from the inner surface of the mouth.

In accordance with another embodiment of the present disclosure, a buttress retention assembly for use with a surgical stapling apparatus includes a buttress material dimensioned to be supported on a jaw member of the surgical stapling apparatus, a base, and a slider. The base defines a first channel configured to receive a distal portion of the jaw member of the surgical stapling apparatus, and a second channel in superposed relation with the first channel. The slider is dimensioned to be slidably received in the second channel. The base is formed of an elastic material such that when the slider is fully received in the second channel of the base, the slider imparts pressure on the first channel to reduce dimensions of the first channel to secure a portion of the buttress material and the distal portion of the jaw member therein.

In an embodiment, the slider may include an elongate engagement portion configured to engage a knife member of the surgical stapling apparatus.

In another embodiment, the slider may include a tapered portion configured to be received in the second channel of the base.

In another embodiment, the second channel may have a tapered profile complementary to the tapered portion of the slider.

In accordance with another embodiment of the present disclosure, a buttress retention assembly for use with a surgical stapling apparatus includes a buttress material dimensioned to be supported on a jaw member of the surgical stapling apparatus, a base, and a lever pivotally mounted on the base. The base defines a first slot configured to receive a portion of the buttress material and a distal portion of the jaw member of the surgical stapling apparatus. The lever is transitionable between a locked state, in which, the lever imparts pressure on the buttress material and the distal portion of the jaw member disposed within the first slot to secure the buttress material and the distal portion of the jaw member to the first slot, and a released position, in which, the buttress material and the distal portion of the jaw member are releasably disposed in the first slot.

In an embodiment, the base may include a hook portion including a finger dimensioned to be received in a knife slot of the jaw member.

In another embodiment, the hook portion may include a transverse member oriented orthogonal to the finger.

In yet another embodiment, the first slot may include a lateral opening to rotatably receive the buttress material and the distal portion of the jaw member therethrough.

In still yet another embodiment, the base may be formed of a flexible material.

BRIEF DESCRIPTION OF THE DRAWINGS

The accompanying drawings illustrate embodiments of the disclosure and, together with a general description of the disclosure given above, and the detailed description of the embodiment(s) given below, serve to explain the principles of the disclosure, wherein.

DETAILED DESCRIPTION

Figure 1:
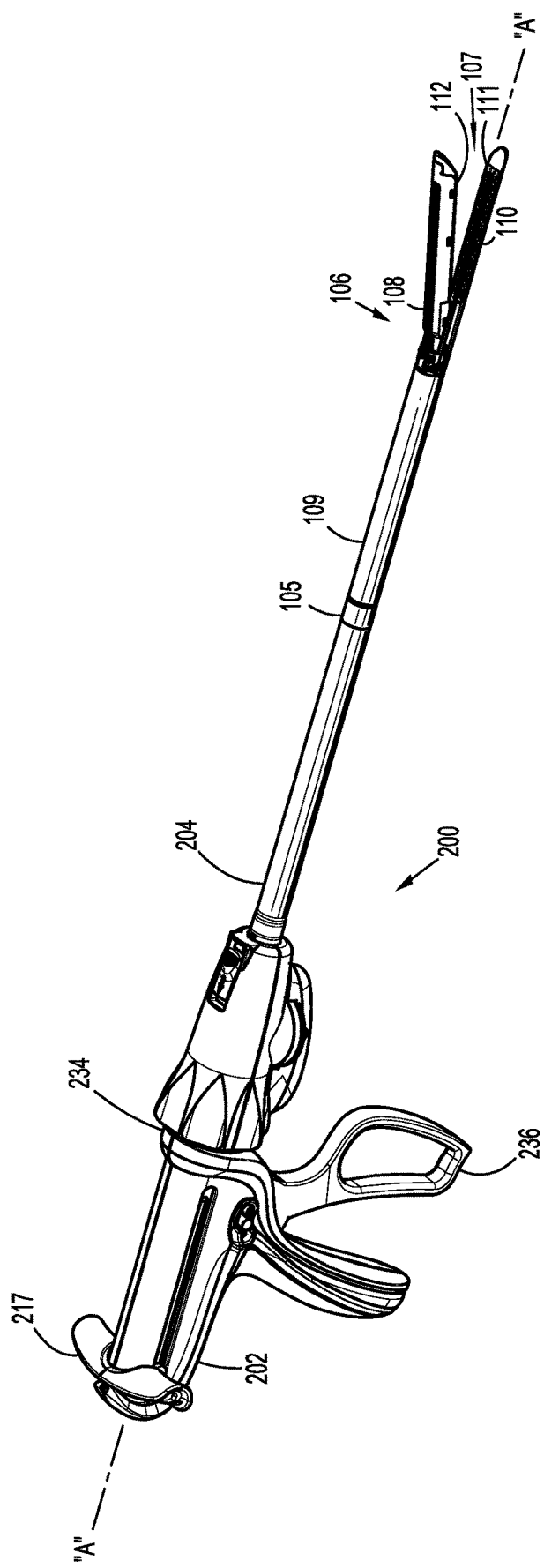
FIG. 1 is a perspective view of a surgical stapling apparatus supporting a reload.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a surgical stapling apparatus 200 for use in stapling tissue and applying a layer of buttress material between staples and underlying tissue. The surgical stapling apparatus 200 generally includes a handle 202 and an elongate tubular member 204 extending distally from the handle 202. The surgical stapling apparatus 200 further includes a retraction mechanism 217 that can be manually grasped and pulled proximally to retract a firing mechanism of the surgical stapling apparatus 200. A reload 106 is removably coupled to a distal end 105 of the elongate tubular member 204. The reload 106 includes a shaft portion 109 and a tool assembly 107 supported on the shaft portion 109. The tool assembly 107 includes first and second jaw members 108, 110 which are movable between an open position for positioning tissue between the first and second jaw members 108, 110 and a closed position for clamping tissue between the first and second jaw members 108, 110 and subsequently stapling tissue. The first jaw member 108 releasably supports a staple cartridge 112, and the second jaw member 110 supports an anvil 111. In any of the embodiments disclosed herein, the tool assembly may 107 be coupled to a mechanical or motorized handle, and the staple cartridge 112 may be removable and replaceable. In any of the embodiments disclosed herein, the reload 106 may be part of a robotic surgical system.

With continued reference to FIG. 1, the surgical stapling apparatus 200 includes a trigger 236 movably mounted on the handle 202. Actuation of the trigger 236 is configured to transition the tool assembly 107 from the open position to the closed position and subsequently actuate the surgical stapling apparatus 200 to apply lines of staples to tissue. In order to provide proper orientation of the tool assembly 107 relative to tissue to be stapled, the surgical stapling apparatus 200 is additionally provided with a rotation knob 234 mounted on the handle 202. Rotation of the rotation knob 234 about a longitudinal axis "A-A" of the surgical stapling apparatus 200 rotates the tool assembly 107 about longitudinal axis "A-A."

Figure 2:
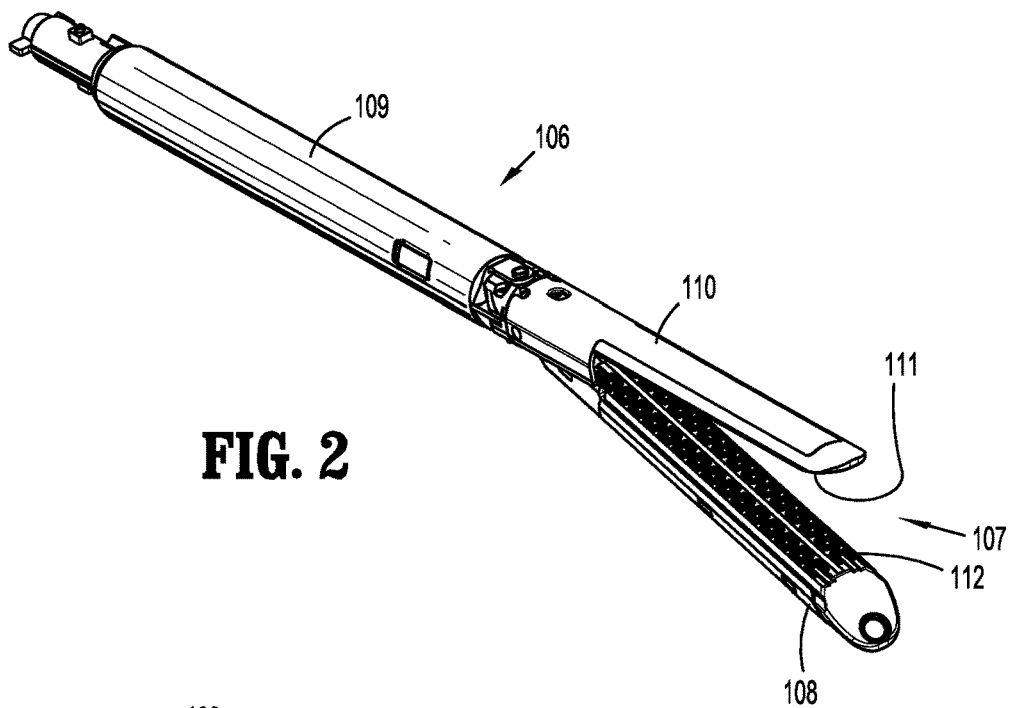
FIG. 2 is a perspective view of the reload of FIG. 1.
Figure 3:
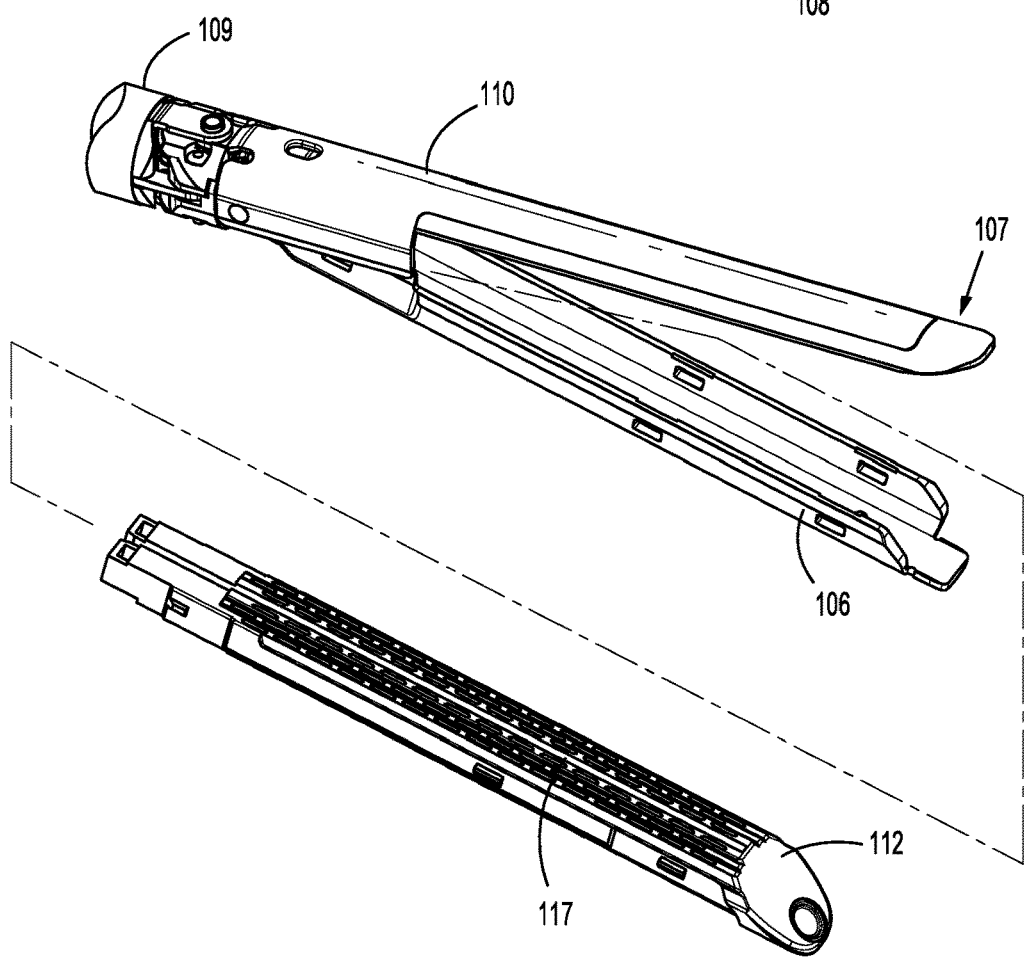
FIG. 3 is a perspective view of a tool assembly of the reload of FIG. 1, illustrating a staple cartridge separated from the tool assembly.

With reference to FIGS. 2 and 3, a driver (not shown) is provided within the reload 106 to move the tool assembly 107 between the open and closed positions. The driver moves along a longitudinal slot 117 defined in the staple cartridge 112. A knife blade 115a (FIG. 11) is associated with the driver to cut tissue captured between the anvil 111 and the staple cartridge 112 as the driver passes through the longitudinal slot 117 defined in the staple cartridge 112. In order to secure the staples provided by the staple cartridge 112 about tissue and a buttress material 300 (FIG. 4), the anvil 111 is provided with longitudinally arranged rows of staple clinching or forming pockets (not shown). Reference may be made to U.S. Patent Application Publication No. 2014/0263550, the entire contents of which are incorporated herein by reference, for a detailed discussion of the construction and operation of the surgical stapling apparatus 200.

Figure 4:
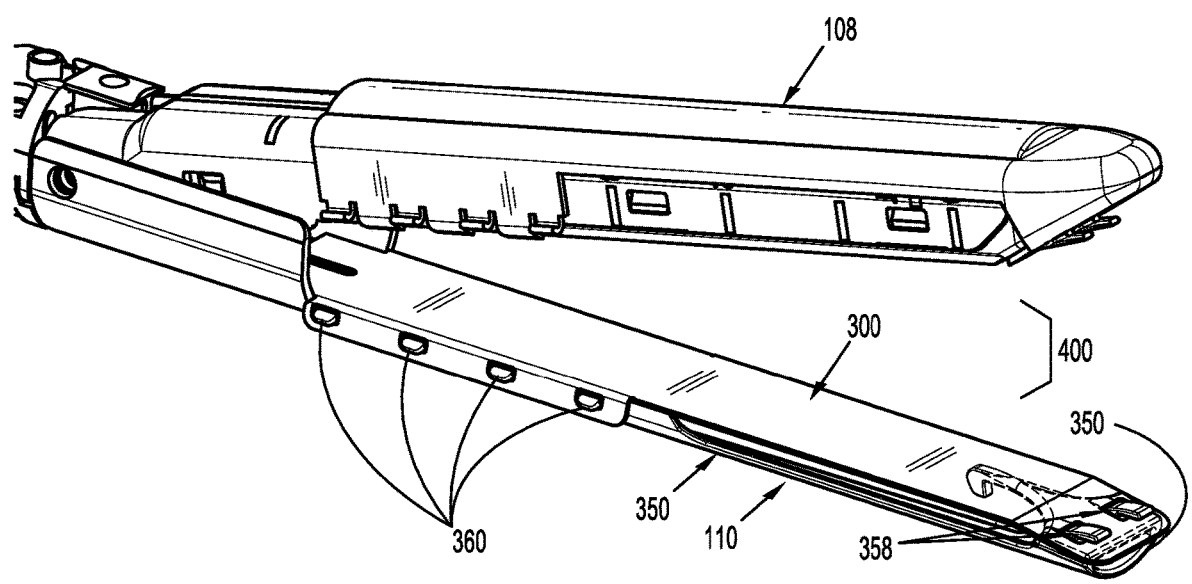
FIG. 4 is a partial perspective view of the tool assembly of FIG. 3 having buttress retention assemblies mounted thereon in accordance with an embodiment of the present disclosure.
Figure 5:
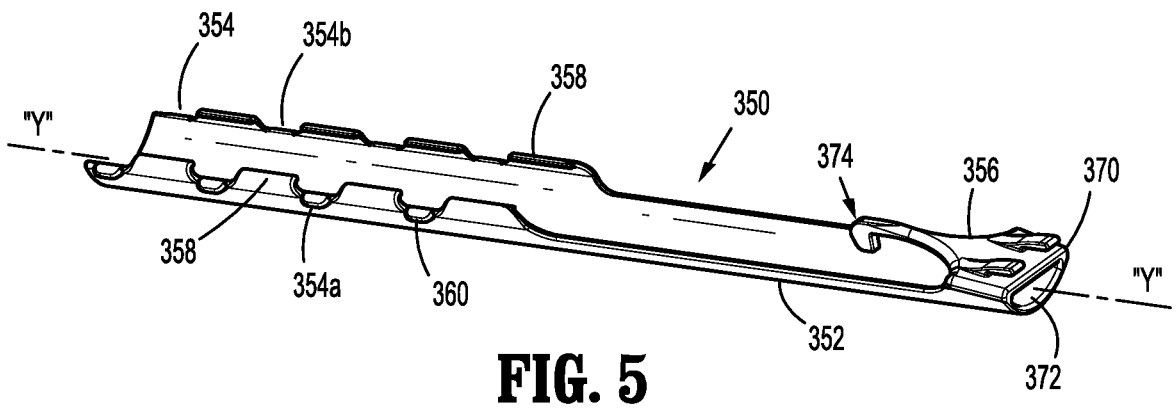
FIG. 5 is a perspective view of a sleeve of the buttress retention assembly of FIG. 4.
Figure 6:
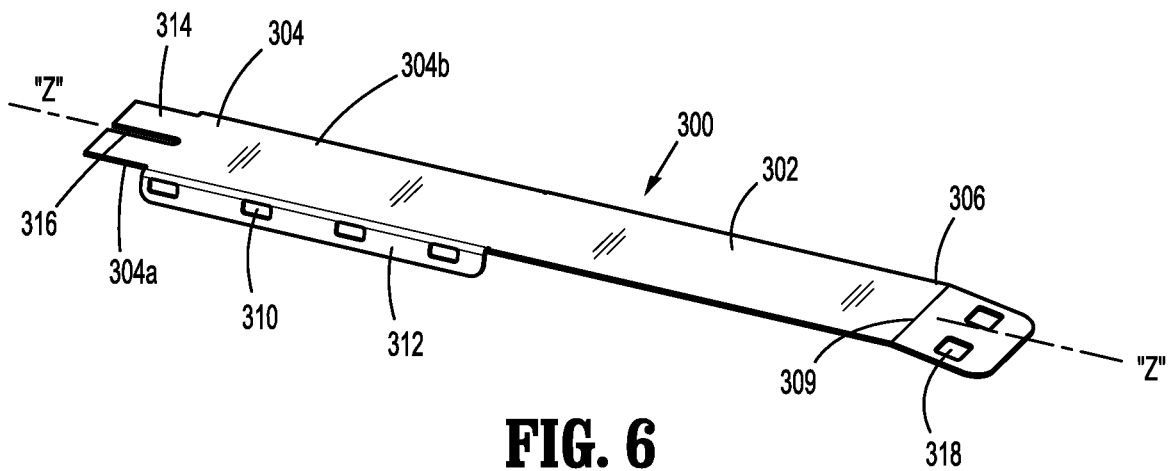
FIG. 6 is a perspective view of a buttress material of the buttress retention assembly of FIG. 4.

With reference now to FIGS. 4-6, there is provided a buttress retention assembly 400 in accordance with an embodiment of the present disclosure. The buttress retention assembly 400 may be adapted for use with the first jaw member 108 including a staple cartridge 112 (FIG. 3) or the second jaw member 110 including the anvil 111 (FIG. 3). In this embodiment, the buttress retention assembly 400 is described with respect to the second jaw member 110 including the anvil 111. The buttress retention assembly adapted for use with the first jaw member 108 is substantially identical to the buttress retention assembly 400 configured for use with the second jaw member 110, and thus, will not be described herein to avoid obscuring the present disclosure in unnecessary detail. The buttress retention assembly 400 includes a buttress material 300 and a sleeve 350 configured to be secured with the second jaw member 110. The buttress material 300 is configured to reinforce and seal staple lines applied to tissue by the surgical stapling apparatus 200 (FIG. 1).

With particular reference to FIG. 5, the sleeve 350 is configured to support the buttress material 300 (FIG. 6) on the second jaw member 110 (FIG. 4). The sleeve 350 may be detachably securable to the second jaw member 110 by, e.g., snap fit or interference fit. The sleeve 350 includes an elongate body 352 configured to receive the second jaw member 110. The elongate body 352 may include an arcuate profile conforming to the contour of the second jaw member 110. The elongate body 352 includes a proximal portion 354 and a distal portion 356. The proximal portion 354 includes a plurality of lips 358 extending transversely outward from lateral sides 354a, 354b of the proximal portion 354. Each lip 358 has an arcuate profile configured to wrap around portions of the second jaw member 110 in order to secure the sleeve 350 to the second jaw member 110. In addition, the proximal portion 354 further includes a plurality of proximal hooks 360 configured to be received in respective proximal slots 310 (FIG. 6) of the buttress material 300. The proximal hooks 360 extend transversely outward from the respective lateral sides 354a, 354b of the proximal portion 354. For example, each proximal hook 360 may be interposed between adjacent lips 358. Each proximal hook 360 may include a detent (not shown) to further secure the buttress material 300 thereto.

With continued reference to FIG. 5, the distal portion 356 of the sleeve 350 includes a mouth 370 having, e.g., an annular structure, defining an aperture 372 dimensioned to receive at least a portion of the buttress material 300 (FIG. 6) therethrough. In particular, the mouth 370 includes a retention hook 374 configured to be received in a knife slot 119 (FIG. 11) of the anvil 111, and distal hooks 358 (shown in phantom in FIG. 4) extending inwardly from an inner wall (not shown) of the mouth 370.

Figure 7:
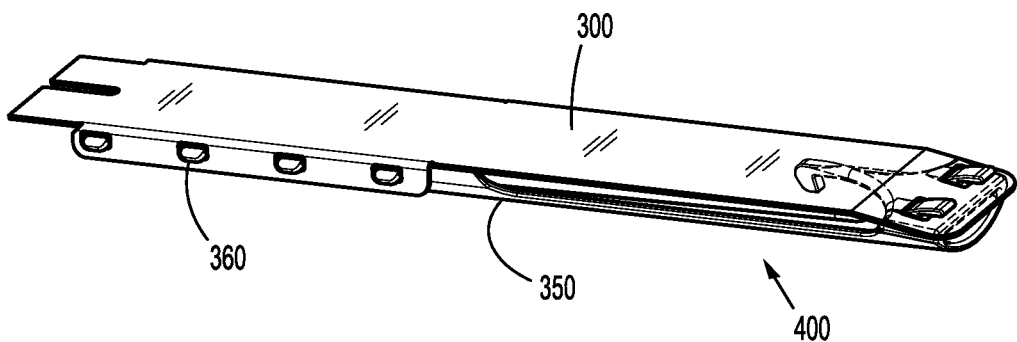
FIG. 7 is a perspective view of a buttress retention assembly of FIG. 4.

With reference now to FIGS. 6 and 7, the buttress material 300 includes an elongate body 302 having a proximal portion 304 and a distal portion 306. The proximal portion 304 is configured to be detachably secured with the proximal portion 354 (FIG. 5) of the sleeve 350. In particular, the proximal portion 304 of the buttress material 300 includes tabs 312 (only one shown) on respective lateral sides 304a, 304b of the proximal portion 304. Each tab 312 includes a plurality of proximal slots 310 configured to receive respective proximal hooks 360 (FIG. 5) of the sleeve 350. The proximal portion 304 further includes a tail portion 314 defining a slit 316 aligned with a longitudinal axis "Z-Z" defined by the elongate body 302 of the buttress material 300. The slit 316 is configured to receive a knife member 115 (FIG. 11) therethrough. The distal portion 306 includes distal slots 318 dimensioned to receive the respective distal hooks 358 (shown in phantom in FIG. 4). The distal portion 306 may also include a partial slit or perforations 309 to facilitate bending of the distal portion 306 relative to the rest of the elongate body 302 of the buttress material 300 in order to improve detachability of the buttress material 300 from the sleeve 350.

Figure 8:
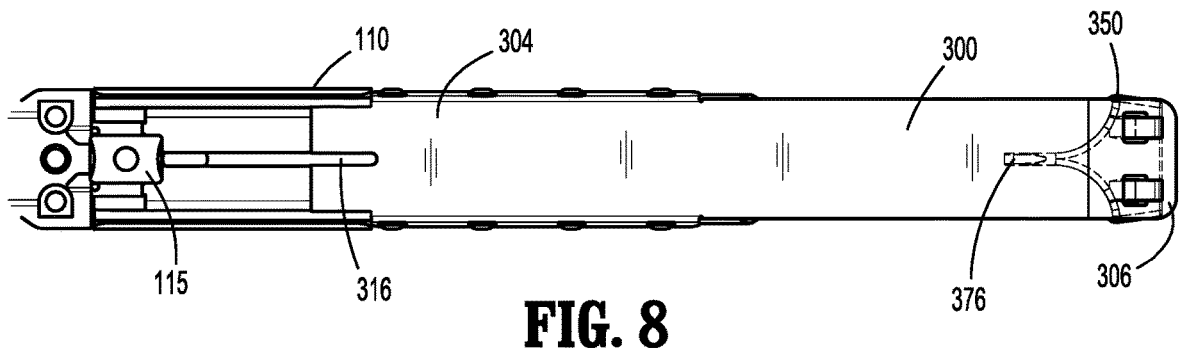
FIG. 8 is a partial top view of the tool assembly of FIG. 1 having the buttress retention assembly mounted thereon.
Figure 9:
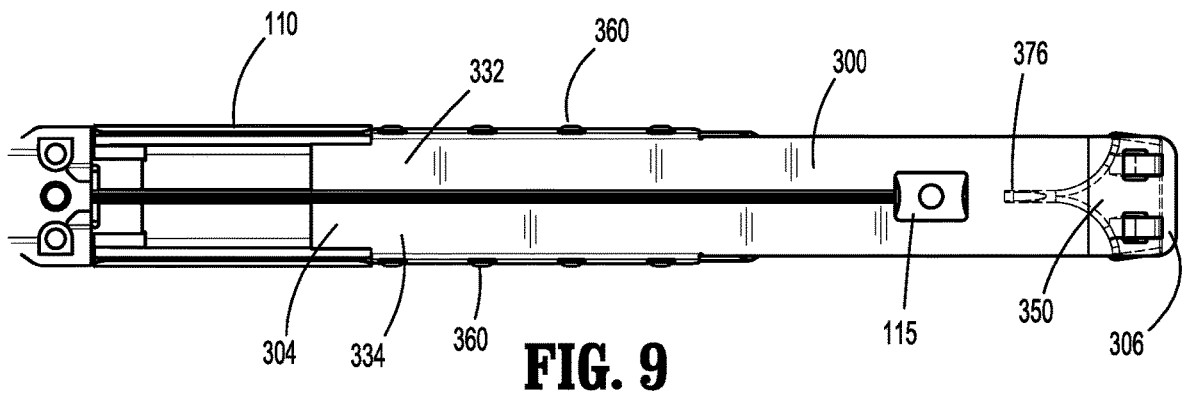
FIGS. 9 and 10 are partial top views of the tool assembly of FIG. 1, illustrating cutting of the buttress material by a knife member.
Figure 10:
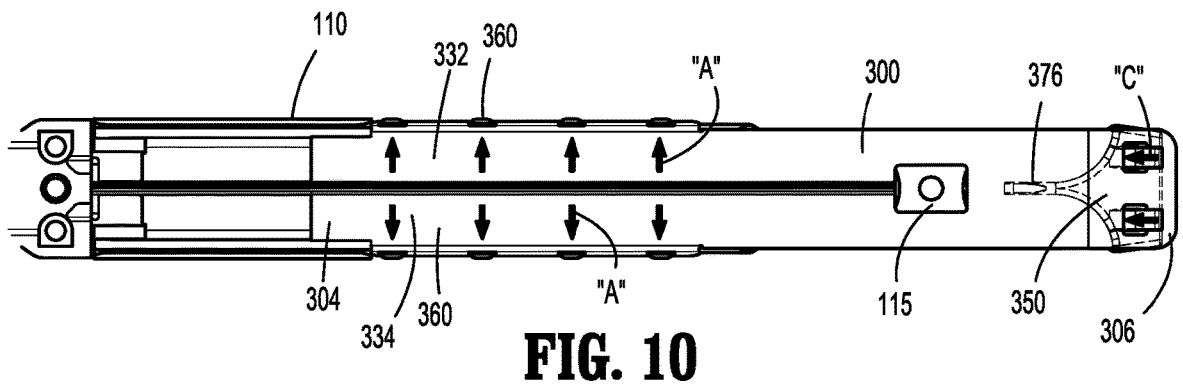

With reference now to FIGS. 8-10, the buttress material 300 is configured to be mounted on the anvil 111 of the second jaw member 110. Once the buttress material 300 is mounted on the anvil 111 of the second jaw member 110, the sleeve 350 is secured with the buttress material 300 and the second jaw member 110. In particular, at least a portion of the distal portion 306 of the buttress material 350 is received through the mouth 370 (FIG. 5) of the sleeve 350 such that the distal hooks 358 (shown in phantom in FIG. 4) of the sleeve 350 is received in the respective distal slots 318 (FIG. 6) of the buttress material 300. Thereafter, the proximal slots 310 (FIG. 6) of the buttress material 300 may be placed over the respective proximal hooks 360 (FIG. 5) of the sleeve 350. In addition, the proximal portion 304 of the buttress material 300 may also be secured to the second jaw member 110 by a suture (not shown), such that when the suture is pulled, the buttress material 300 may be displaced proximally to aid placement of the proximal hook 360 through the proximal slots 310. A suture attachment method as disclosed in WO 2008/109125, the disclosure of which is hereby incorporated by reference herein, can be used. Under such a configuration, the retention hook 374 of the sleeve 350 is received in the knife slot 119 (FIG. 11) of the anvil 111, which, in turn, urges the buttress material 300 inward towards the knife slot 119 defined in the anvil 111. When the buttress material 300 is supported on the anvil 111, the slit 316 of the buttress material 300 is aligned with the knife slot 119 (FIG. 11) of the anvil 111.

With particular reference to FIGS. 9 and 10, when the knife member 115 (FIG. 11) travels through the knife slot 119 (FIG. 11) of the anvil 111 and cuts through the buttress material 300, the resulting first and second portions 332, 334 of the buttress material 300 extend transversely outward in the direction of arrows "A" such that the proximal hooks 360 (FIG. 5) of the sleeve 350 are released from the respective proximal slots 310 (FIG. 6) of the buttress material 300. Once the knife member 115 travels through the proximal portion 304 of the buttress material 300, e.g., distal of the tabs 312 (FIG. 6), the retention hook 374 of the sleeve 350 continues to apply force against the buttress material 300. However, in the absence of the proximal hooks 360 inhibiting axial and transverse displacement of the buttress material 300 relative to the sleeve 350, the distal hooks 358 (shown in phantom in FIG. 4) are released from the respective distal slots 318 (FIG. 6) of the buttress material 300. The first and second jaw members 108, 110 may be displaced proximally, which, in turn, releases the buttress material 300 now attached to a stapled tissue, from the sleeve 350.

Figure 11:
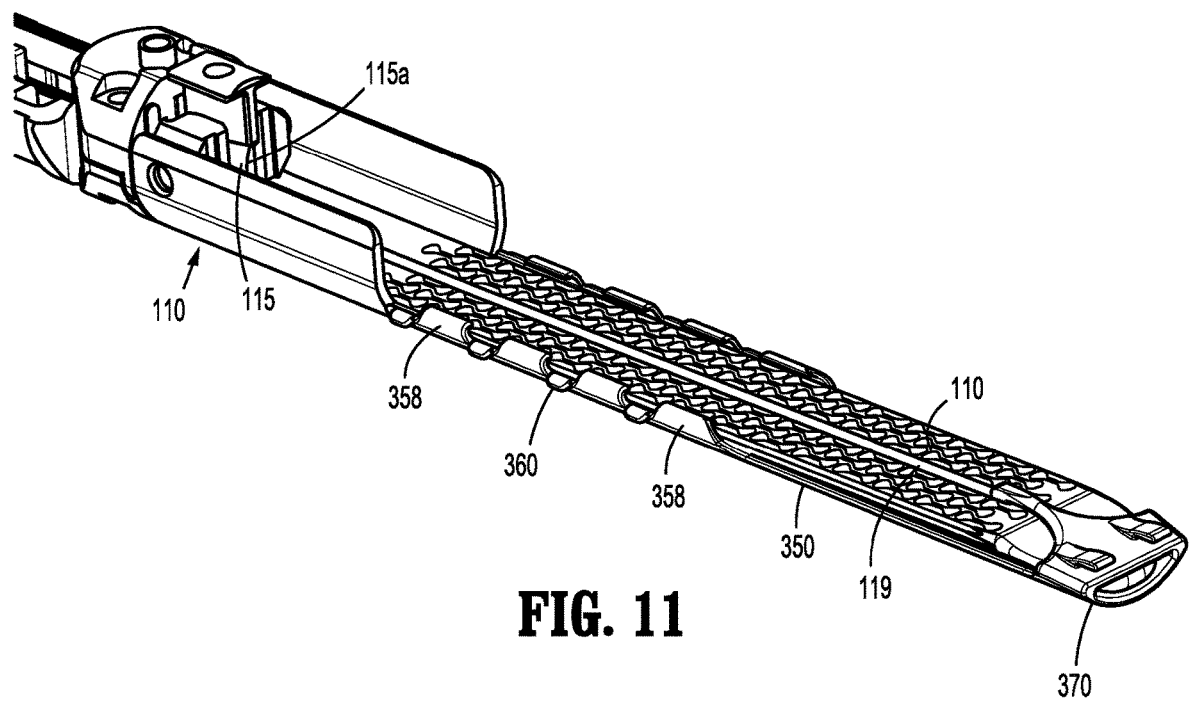
FIGS. 11 and 12 are partial perspective views of the tool assembly of FIG. 3, illustrating a sleeve mounted on the jaw member without the buttress material.
Figure 12:
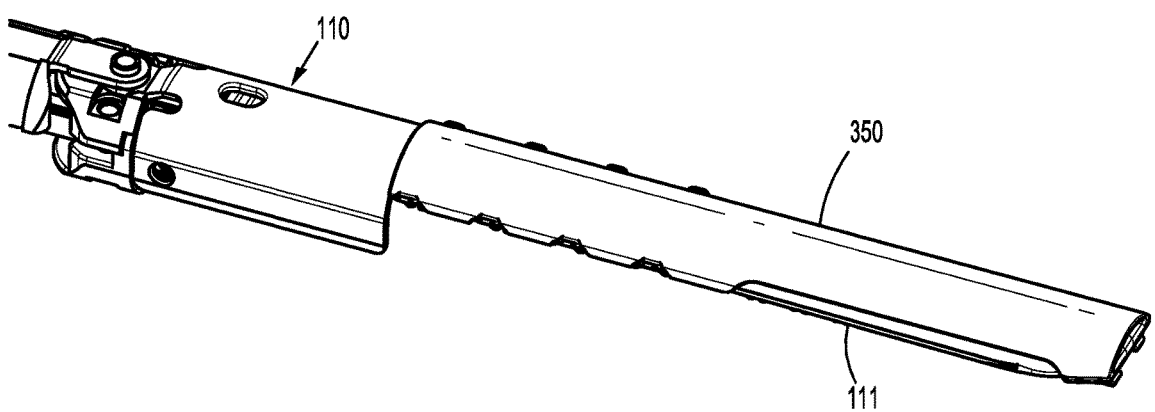

With reference to FIGS. 11 and 12, after the staples have been applied to the tissue, the buttress material 300 is detached from the sleeve 350 without leaving any unused portions or residual buttress material 300. At this time, a new buttress material 300 may be loaded on the sleeve 350 and the second jaw member 110.

It is further contemplated that the buttress materials 300 may be made from any biocompatible natural or synthetic material. The material from which the buttress material is formed may be bioabsorbable or non-bioabsorbable. It should of course be understood that any combination of natural, synthetic, bioabsorbable and non-bioabsorbable materials may be used to form the buttress material.

Some non-limiting examples of materials from which the buttress material may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the buttress material. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material.

The buttress material may be porous or non-porous, or combinations of porous and non-porous layers. Where the buttress material is non-porous, buttress material may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like.

In embodiments, the buttress material is porous and possesses hemostatic properties. Where the buttress material is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where the buttress material is porous, the pores may be formed using any method suitable to forming a foam or sponge including, but not limited to the lyophilization or freeze-drying of a composition. Suitable techniques for making foams are within the purview of those skilled in the art. Porous buttress materials can be at least 0.2 cm thick, in embodiments from about 0.3 to about 1.5 cm thick. Porous buttress materials can have a density of not more than about 75 mg/cm' and, in embodiments below about 20 mg/cm$^2$. The size of the pores in the porous buttress materials can be from about 20 μm to about 300 in embodiments from about 100 μm to about 200 μm.

The buttress material may also include a reinforcement member. The reinforcement member may be associated with a porous or non-porous layer or may be positioned between a non-porous layer and a porous layer of the buttress material. Alternatively, the reinforcement member may be positioned entirely within one or more of the individual layers (e.g., embedded within the porous layer, the non-porous layer, or both) of the buttress material. It is also envisioned that the reinforcement member may be positioned at the surface of one of the layers making up the buttress material and, in embodiments, may be positioned at an exterior surface of the buttress material.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the buttress material has randomly oriented chopped fibers that have not been previously fused together embedded within in the buttress material.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect such as a compound that affects or participates in tissue growth, cell growth, or cell differentiation.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly (vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the buttress material in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-viral s; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

In use, the staple cartridge 112 is loaded in the first jaw member 108. Thereafter, the buttress retention assembly 400 is assembled with the second jaw member 110 including the anvil 111. Optionally, the buttress retention assembly adapted for use on the first jaw member 108 may be used. The proximal portion 304 of the buttress material 300 may be secured to the second jaw member 110 by a suture such that when the suture is pulled, the buttress material 300 is displaced proximally. The distal portion 306 of the buttress material 300 is received in the mouth 370 of the sleeve 350 such that the distal hooks 358 of the sleeve 350 are received in the respective distal slots 318 of the buttress material 300. Thereafter, the suture may be pulled to displace the buttress material 300 proximally, or alternatively, the buttress material 300 may be pulled proximally, to place the proximal hooks 360 of the sleeve 350 through the respective proximal slots 310 of the buttress material 300.

At this time, the tool assembly 107 is positioned adjacent tissue to be stapled. The driver (not shown) is in a proximal position relative to the longitudinal slot 117 of the staple cartridge 112. The staple cartridge 112 includes the staples positioned within the respective staple pockets. The staples are of a conventional type and include a backspan having a pair of legs extending from the backspan. The legs terminate in tissue penetrating tips. Pushers are located within respective staple pockets and are positioned between the staples and the path of a drive bar.

The surgical stapling apparatus 200 is initially actuated by movement of the trigger 236 relative to the handle 202 causing the driver to move distally, thereby transitioning the tool assembly 107 to the closed position. The drive bar advances distally and urges the pushers upwardly against the backspans of the staples, thereby driving the staples through tissue and the buttress material 300 mounted on the contact surface 111a of the anvil 111. The tissue penetrating tips of the staples are bent within the staple clinching pockets in the anvil 111 to thereby secure the buttress material 300 mounted on the anvil 111 against tissue, while the backspan may secure the buttress material 300 optionally mounted on the staple cartridge 112 against tissue.

Upon full actuation of the surgical stapling apparatus 200, the knife blade 115a associated with the surgical stapling apparatus 200 and carried by the driver cuts tissue, as well as the buttress materials 300 on opposing sides of tissue, between the rows of now clinched staples. The resulting tissue is divided and stapled with the staples. Specifically, the buttress material 300 that may be optionally mounted on the staple cartridge 112 may be secured against tissue by the backspans of the staples, and the buttress material 300 mounted on the anvil 111 is secured against tissue by the now clinched tissue penetrating tips of the staples. In this manner, the buttress materials 300 may be stapled to tissue thereby sealing and reinforcing the staple lines created by the staples.

As the knife member 115 advances distally, the buttress material 300 is split into first and second portions 332, 334, which, in turn, causes the tabs 312 of the buttress material 300 to move transversely outward. In this manner, the tabs 312 are released from the proximal hooks 360 of the sleeve 350. As the knife member 115 is advanced distal of the proximal hooks 360 of the sleeve 350, the distal hooks 358 of the sleeve 350 are released from the buttress material 300 as the retention hook 374 of the sleeve 350 urges the buttress material 300 inward towards the knife slot 119 of the anvil 111. At this time, the clinician may move the first and second jaw members 108, 110 proximally in order to detach the buttress material 300 stapled to tissue, from the tool assembly 107.

The spent cartridge is then removed and a fresh cartridge and a new buttress material 300 can be loaded onto the reload 106. A reload with a removable and replaceable staple cartridge is disclosed in U.S. Pat. No. 9,016,539, the disclosure of which is hereby incorporated by reference herein.

Figure 13:
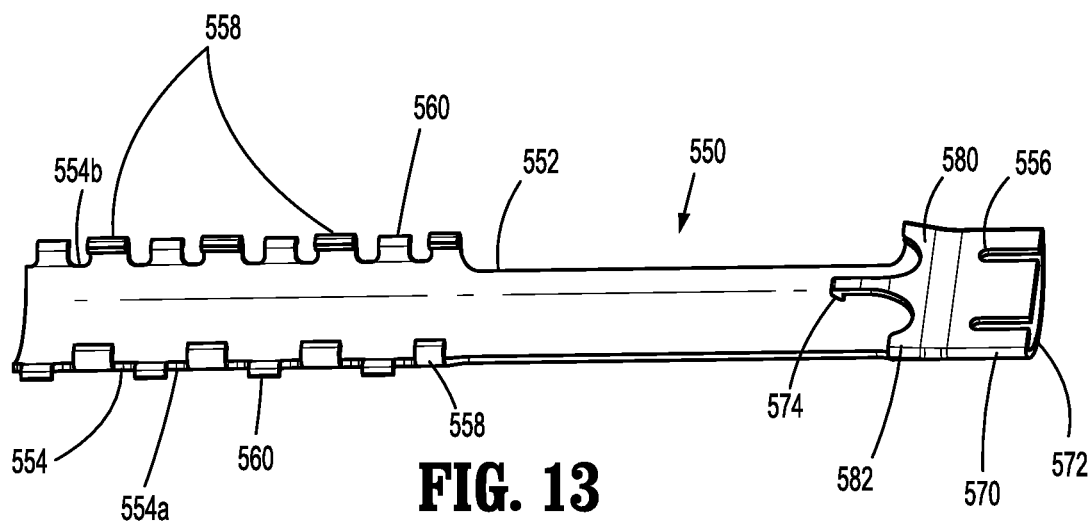
FIG. 13 is a perspective view of a sleeve for use with the tool assembly of FIG. 1 in accordance with another embodiment of the present disclosure.

With reference to FIG. 13, another embodiment of a sleeve for use with the buttress material 300 is shown as a sleeve 550. Parts of the sleeve 550 substantially identical to those of the sleeve 350 will not be described herein to avoid obscuring the present disclosure in unnecessary detail. The sleeve 350 may be detachably secured to the second jaw member 110 (FIG. 1) by, e.g., snap fit or interference fit. In particular, the sleeve 550 includes an elongate body 552 configured to receive the second jaw member 110. The elongate body 552 may include an arcuate profile conforming to the contour of the second jaw member 110. The elongate body 552 includes a proximal portion 554 and a distal portion 556. The proximal portion 554 includes a plurality of lips 558 extending transversely outward from opposing lateral sides 554a, 554b of the proximal portion 554. Each lip 558 has an arcuate profile configured to wrap around portions of the second jaw member 110 in order to secure the sleeve 550 to the second jaw member 110. In addition, the proximal portion 554 further includes a plurality of proximal hooks 560 configured to be received in respective proximal slots 310 (FIG. 6) of the buttress material 300. Each proximal hook 560 extends transversely outward from the opposing lateral sides 554a, 554b of the proximal portion 554. For example, each proximal hook 560 may be interposed between adjacent lips 558.

With continued reference to FIG. 13, the distal portion 556 of the sleeve 550 includes a mouth 570 having, e.g., an annular structure, defining an aperture 572 dimensioned to receive at least a portion of the buttress material 300 therethrough. In particular, the mouth 570 includes a retention hook 574 configured to be received in the knife slot 119 (FIG. 11) of the anvil 111, and distal hooks (not shown) extending inwardly from an inner wall (not shown) of the mouth 570.

The distal portion 556 of the sleeve 550 further includes a nose portion 580 including opposing sides 582 operatively coupled with the retention hook 574 such that when the opposing sides 582 of the nose portion 580 are squeezed together by the clinician, the retention hook 574 is displaced away from the knife slot 119 when the sleeve 550 is supported on the second jaw member 110. Displacement of the retention hook 574 away from the knife slot 119 facilitates loading or unloading of the buttress material 300. It is contemplated that the sleeve 550 may be adapted for use with the first jaw member 108 including the staple cartridge 112. The method of use of the sleeve 550 is substantially identical to that of the sleeve 350, and thus, will not be described herein.

Figure 14:
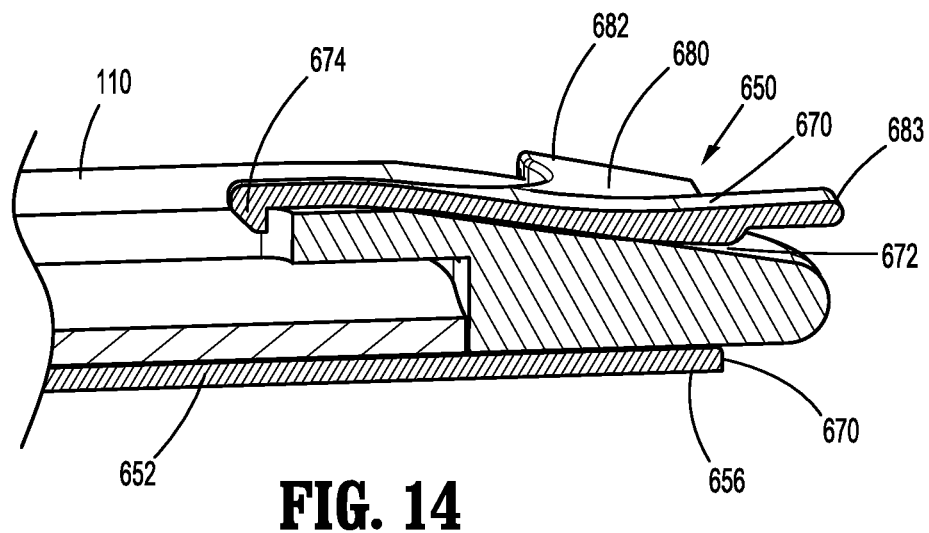
FIG. 14 is a partial perspective view of a sleeve for use with the tool assembly of FIG. 1 in accordance with another embodiment of the present disclosure.

With reference to FIG. 14, another embodiment of a sleeve for use with the buttress material 300 is shown as a sleeve 650. Parts of the sleeve 650 identical to those of the sleeve 550 will not be described herein in order to avoid obscuring the present disclosure in unnecessary detail. The sleeve 650 may be detachably secured to the second jaw member 110 by, e.g., snap fit or interference fit. In particular, the sleeve 650 includes an elongate body 652 configured to receive the second jaw member 110.

Figure 15:
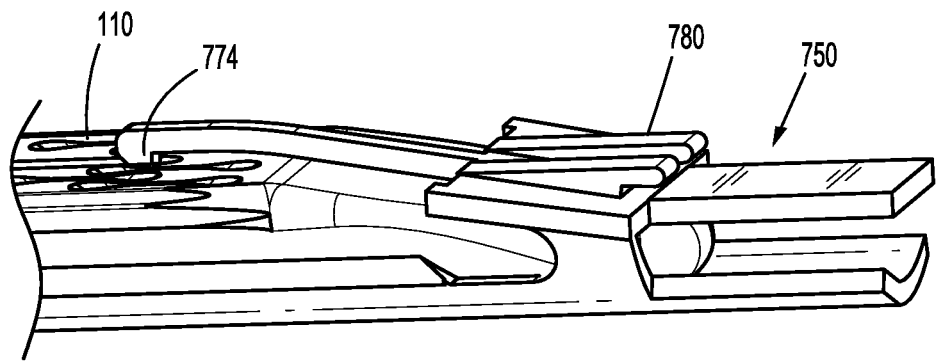
FIG. 15 is a partial perspective view of a sleeve for use with the tool assembly of FIG. 1 in accordance with another embodiment of the present disclosure.

The distal portion 656 of the sleeve 650 includes a mouth 670 having, e.g., an annular structure, defining an aperture 672 dimensioned to receive at least a portion of the buttress material 300 therethrough. In particular, the mouth 670 includes a retention hook 674 configured to be received in the knife slot 119 (FIG. 11) of the anvil 111. The distal portion 656 of the sleeve 650 includes a nose portion 680 including opposing sides 682 (only one side shown) operatively coupled with the retention hook 674 such that when the opposing sides 682 of the nose portion 680 are squeezed together by the clinician, the retention hook 674 is displaced away from the knife slot 119 when the sleeve 650 is supported on the second jaw member 110. In addition, the sleeve 650 may further include a lever 683 operatively coupled with the retention hook 674 and extending distally from the nose portion 680 such that when the clinician presses the lever 683 towards the anvil 111, the retention hook 674 is displaced away from the knife slot 119. Loading and unloading of the buttress material 300 to and from the second jaw member 110 is facilitated by use of the nose portion 680 and the lever 683. As can be appreciated with reference to FIG. 15, a sleeve 750 may include a lever 780 operatively coupled with a retention hook 774 without a nose portion configured to be squeezed by the clinician to displace the retention hook 774, as disclosed in the sleeves 550, 650. It is contemplated that the sleeves 650, 750 may be tailored for use with the first jaw member 108 including the staple cartridge 112. The method of use of the sleeves 650, 750 is substantially identical to that of the sleeve 350, and thus, will not be described herein.

Figure 16:
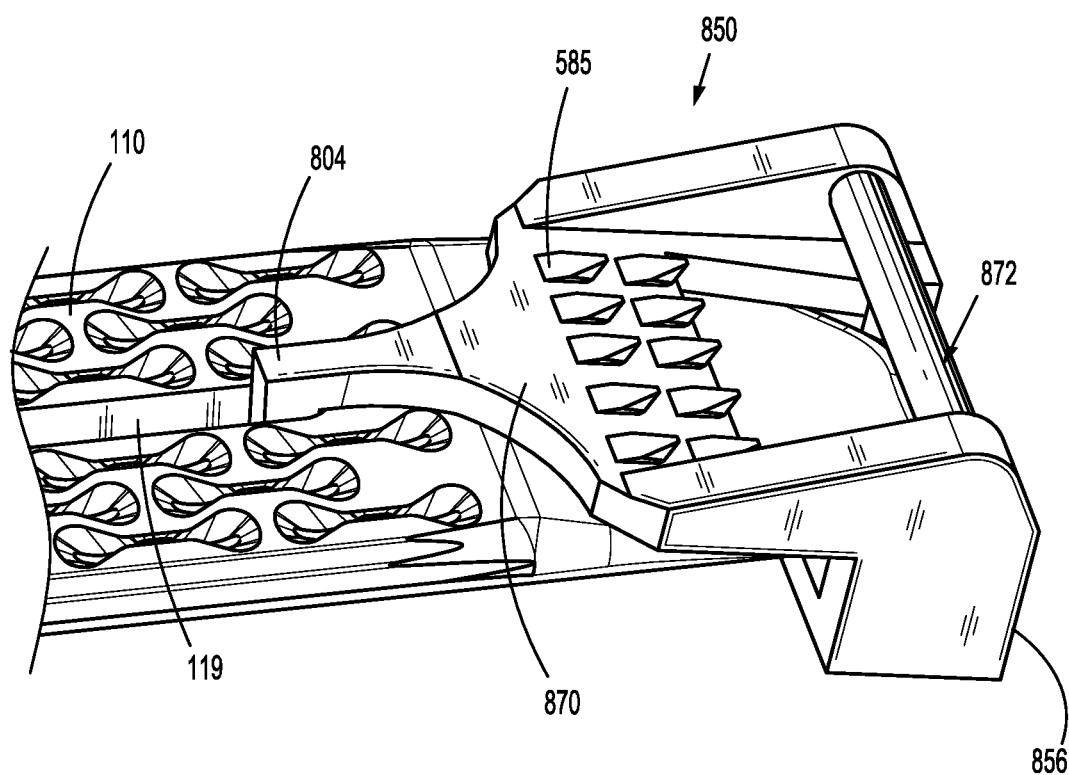
FIG. 16 is a buttress retention assembly for use with the tool assembly of FIG. 1 in accordance with another embodiment of the present disclosure.

With reference to FIG. 16, another embodiment of a sleeve for use with the buttress material 300 is shown as a sleeve 850. Parts of the sleeve 850 substantially identical to those of the sleeve 350 will not be described herein to avoid obscuring the present disclosure in unnecessary detail. The sleeve 850 may be detachably secured to the second jaw member 110 by, e.g., snap fit or interference fit. In particular, the sleeve 850 is configured to receive the second jaw member 110. The sleeve 850 includes a distal portion 856.

With continued reference to FIG. 16, the distal portion 856 of the sleeve 850 includes a base 870 defining an aperture 872 dimensioned to receive at least a portion of the buttress material 300 therethrough. At least a portion of the base 870 defines an acute angle with respect to the anvil 111 when assembled with the anvil 111. In particular, the base 870 includes a retention hook 874 configured to be received in the knife slot 119 of the anvil 111, and distal hooks 585 extending towards the anvil 111. The distal hooks 585 may extend from the portion of the base 870 that defines the acute angle with respect to the anvil 111. Under such a configuration, the angled portion of the base 870 may facilitate detachable securement of the buttress material 300 thereto. It is contemplated that the sleeve 850 may be tailored for use with the first jaw member 108 including the staple cartridge 112. The method of use of the sleeve 850 is substantially identical to that of the sleeve 350, and thus, will not be described herein.

Figure 17:
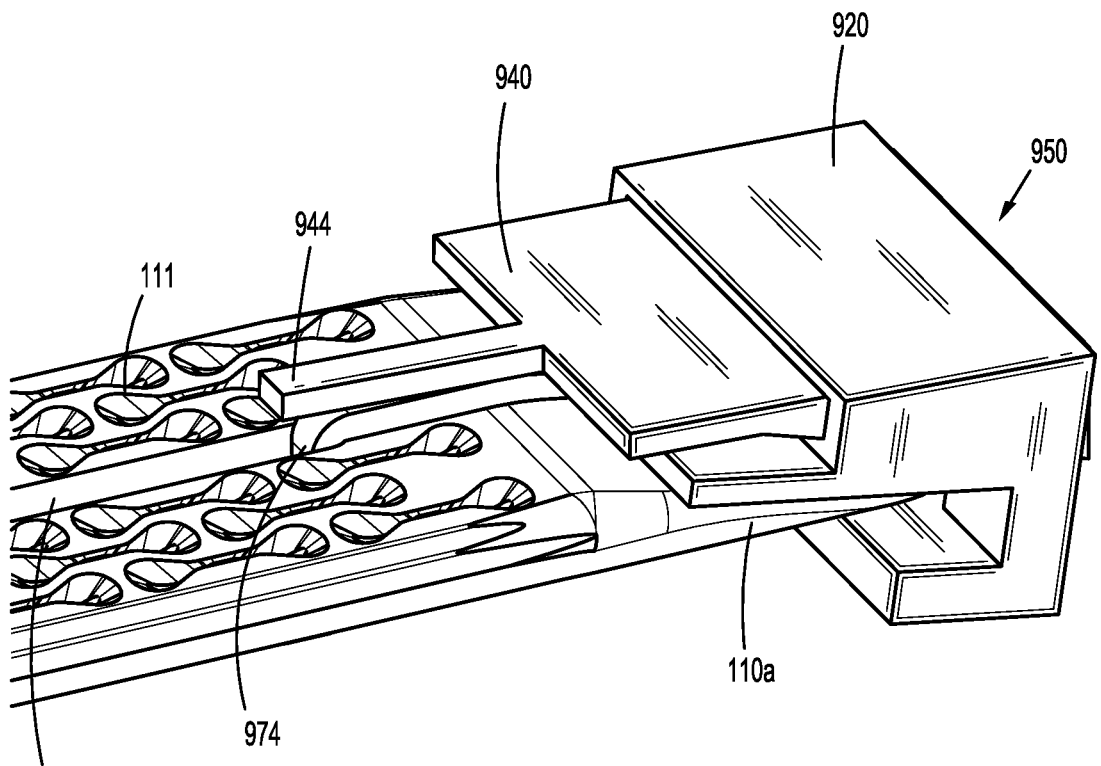
FIGS. 17-19 are perspective views of a buttress retention assembly in accordance with another embodiment of the present disclosure.
Figure 18:
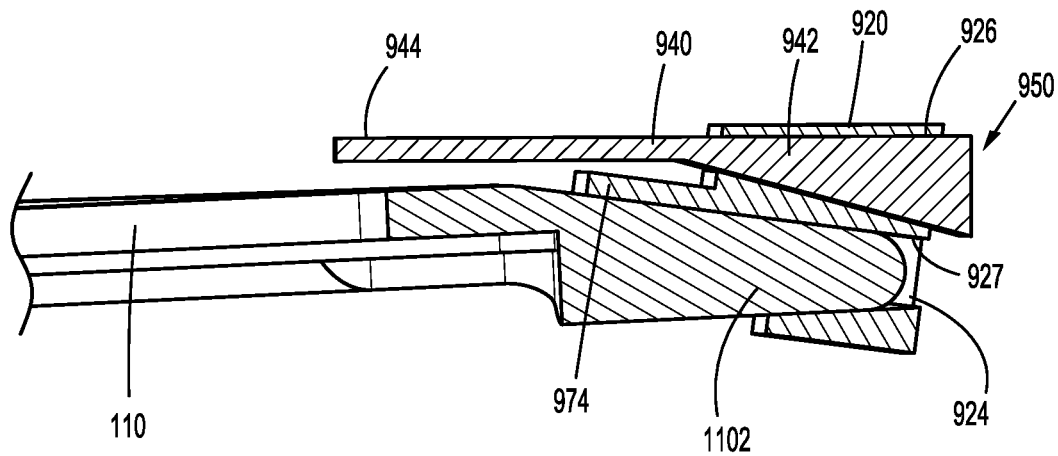
Figure 19:
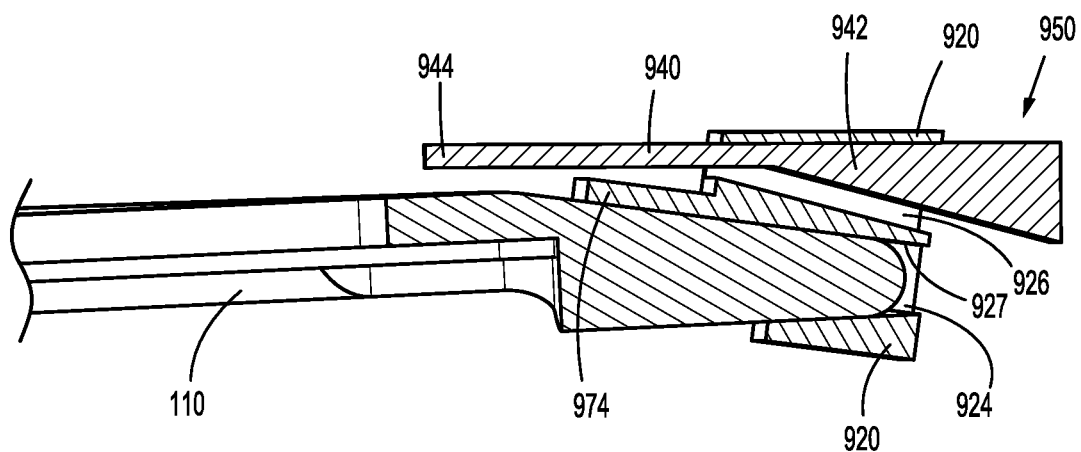

With reference now to FIGS. 17-19, there is illustrated a distal latch assembly 950 configured to detachably support the buttress material 300 (FIG. 6) on the second jaw member 110 including the anvil 111. However, it is also contemplated that the distal latch assembly 950 may be adapted for use with the first jaw member 108 including the staple cartridge 112. The distal latch assembly 950 includes a base 920 configured to engage a distal end 110a of the second jaw member 110. The distal latch assembly 950 includes a retention hook 974 configured to be positioned in the knife slot 119 of the anvil 111 to urge the buttress material 300 towards the knife slot 119 of the anvil 111. The base 920 defines a first channel 924 dimensioned to receive at least a portion of the distal end 110a of the second jaw 110, and a second channel 926 proximally tapered to slidably receive a slider 940 therein. The base 920 is formed of a flexible material such that when a tapered portion 942 of the slider 940 is fully positioned in the second channel 926 of the base 920, the slider 940 causes an inner wall 927 of the base 920 to impart pressure on the distal end 110a of the second jaw member 110 disposed in the first channel 924. In this manner, when the slider 940 fully engages the second channel 926, the buttress material 300 is secured between the second jaw member 110 and the inner wall 927 of the base 920 defining the first channel 924. The slider 940 and the second channel 926 are configured such that when the slider 940 is moved distally, e.g., the slider 940 partially engages the inner wall 927 of the base 920, the slider 940 imparts less pressure on the buttress material 300 disposed in the first channel 924. In this manner, when the knife member 115 is actuated distally, the knife member 115 engages the engagement portion 944 of the slider 940, and imparts distal movement to the slider 940, thereby reducing the pressure applied to the buttress material 300 by the inner wall 927 defining the first channel 924. Under such a configuration, the buttress material 300 may be secured to the anvil 111 during the operation of the surgical stapling apparatus 200, and releasable at the end of the stapling process.

In use, the buttress material 300 is positioned on the anvil 111. The proximal portion 304 of the buttress material 300 may be secured with the second jaw member 110 by using a suture as described hereinabove. Prior to securing the buttress material 300 to the anvil 111, the slider 940 is moved in a distal-most position to facilitate receipt of the distal end 110a of the second jaw member 110 into the first channel 924 of the base 920. At this time, the distal end 110a of the second jaw member 110 is received in the first channel 924 such that the buttress material 300 engages the inner wall 927 of the base 920 defining the first channel 924. Thereafter, the slider 940 is displaced proximally in order to apply pressure on the buttress material 300 in the first channel 924, to thereby secure the buttress material 300 thereto. Once the buttress material 300 is secured with the second jaw member 110, the surgical stapling apparatus 200 may be actuated to perform stapling of tissue, as described hereinabove. Upon completion of the stapling of tissue, the buttress material 300 now attached to tissue may be detached from the second jaw member 110 through the disengagement (or partial engagement) of the slider 940 from the second channel 926.

Figure 20:
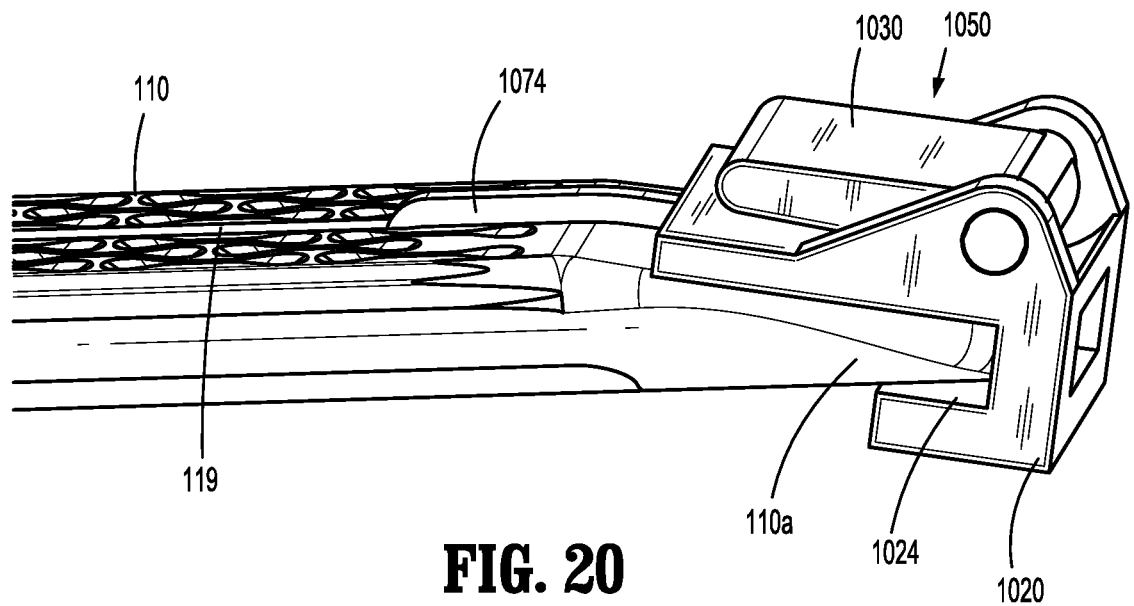
FIG. 20 is a perspective view of a buttress retention assembly in accordance with another embodiment of the present disclosure.

With reference to FIG. 20, another embodiment of a distal latch assembly configured to detachably support the buttress material 300 on the anvil 111 is generally shown as a distal latch assembly 1050. However, it is also contemplated that the distal latch assembly 1050 may be adapted for use with the first jaw member 108 including the staple cartridge 112. The distal latch assembly 1050 includes a base 1020 configured to engage the distal end 110a of the second jaw member 110. The distal latch assembly 1050 includes a retention hook 1074 configured to be positioned in the knife slot 119 of the anvil 111 to urge the buttress material 300 inward towards the knife slot 119 when the buttress material 300 is disposed on the anvil 111. The base 1020 defines a slot 1024 dimensioned to receive at least a portion of the distal end 110a of the second jaw member 110. The distal latch assembly 1050 further includes a lever 1030 pivotably associated with the base 1020. The base 1020 is formed of a flexible material such that when the lever 1030 is in a locked position, the lever 1030 imparts pressure on the base 1020, which, in turn, applies pressure to the distal end 110a of the second jaw member 110 disposed in the slot 1024, and when the lever 1030 is in a released position, the lever 1030 does not impart pressure on the base 1020. Under such a configuration, the buttress material 300 disposed on the distal end 110a of the second jaw member 110 may be secured against the base 1020 by placing the lever 1030 in the locked position, and may be released from the base 1020 by placing the lever 1030 in the released position. The method of use of the distal latch assembly 1050 is substantially identical to those described hereinabove, and thus, will not be described.

Figure 21:
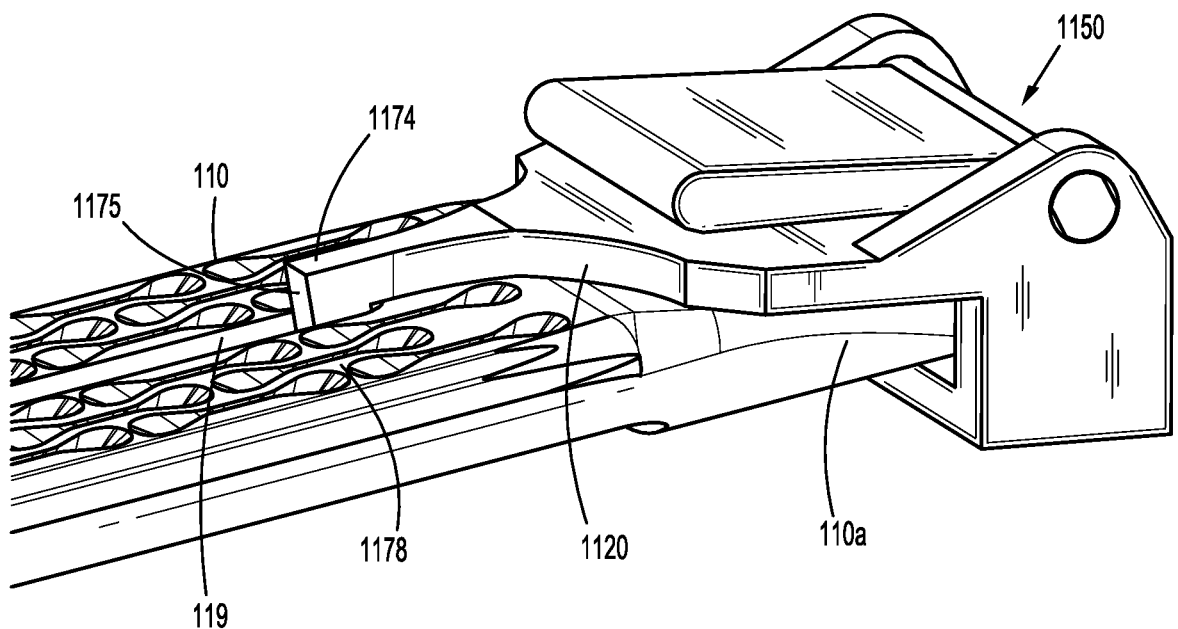
FIGS. 21 and 22 are perspective views of a buttress retention assembly in accordance with yet another embodiment of the present disclosure.
Figure 22:
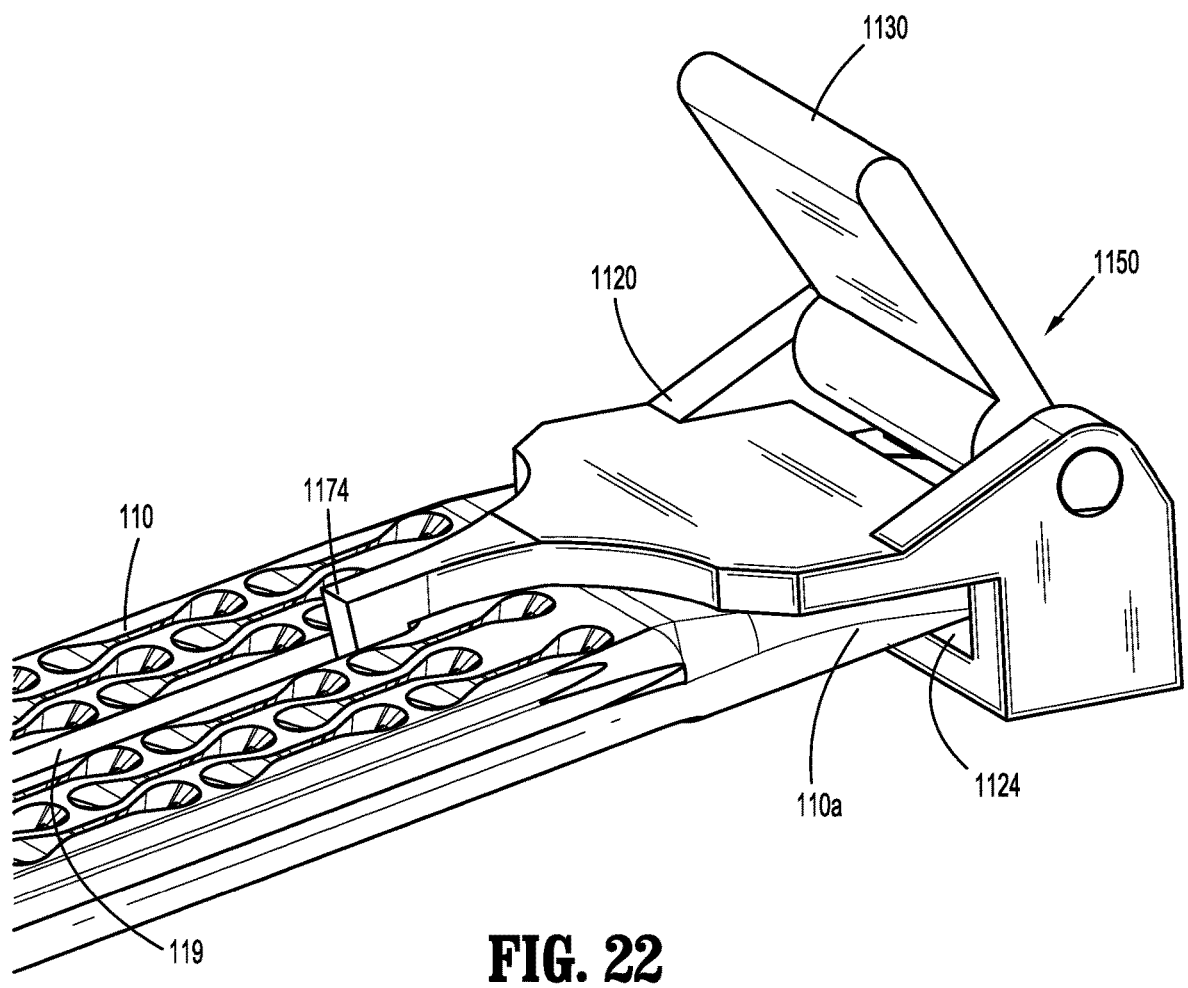

With reference to FIGS. 21 and 22, another embodiment of a distal latch assembly configured to detachably support the buttress material 300 on the second jaw member 110 including the anvil 111 is generally shown as a distal latch assembly 1150. However, it is also contemplated that the distal latch assembly 1150 may be adapted for use with the first jaw member 108 including the staple cartridge 112. Parts of the distal latch assembly 1150 identical to those of the distal latch assembly 1050 will not be described to avoid obscuring the present disclosure in unnecessary detail.

The distal latch assembly 1150 includes a base 1120 configured to engage the distal end 110a of the second jaw member 110. The distal latch assembly 1150 includes a retention hook 1174 configured to be positioned in the knife slot 119 of the anvil 111 to urge the buttress material 300 inward towards the knife slot 119 when the buttress material 300 is disposed on the anvil 111. In particular, the retention hook 1174 includes a hook member 1175 dimensioned to be received in the knife slot 119 of the anvil 111, and a transverse member 1178 (shown in phantom in FIG. 21) disposed orthogonal to the hook member 1175. Under such a configuration, in order to place the retention hook 1174 into the knife slot 119 of the anvil 111, the transverse member 1178 is first aligned with the knife slot 119 and thereafter positioned in the knife slot 119 of the anvil 111. The retention hook 1174 is then rotated about 90 degrees such that the transverse member 1178 is orthogonal to the knife slot 119, thereby providing additional securement of the distal latch assembly 1150 to the second jaw member 110. The base 1120 defines an aperture 1124 dimensioned to receive at least a portion of the distal end 110a of the second jaw member 110. The distal latch assembly 1150 further includes a lever 1130 pivotably associated with the base 1120. The base 1120 is formed of a flexible material such that when the lever 1130 is in a locked position, the lever 1130 imparts pressure on the base 1120, which, in turn, applies pressure to the distal end 110a of the second jaw member 110 disposed in the slot 1124, and when the lever 1130 is in a released position, the lever 1130 does not impart pressure on the base 1120. Under such a configuration, the buttress material 300 disposed on the anvil 111 may be secured against the base 1120 by placing the lever 1130 in the locked position, and may be released from the base 1120 by placing the lever 1130 in the released position. The method of use of the distal latch assembly 1150 is substantially identical to those described hereinabove, and thus, will not be described.

Figure 23:
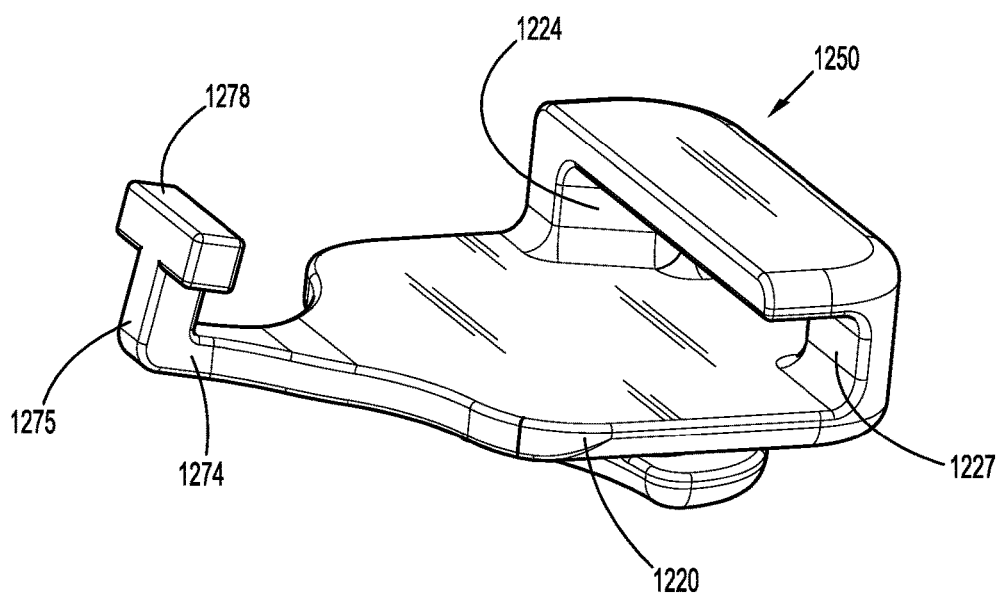
FIG. 23 is a bottom perspective view of a buttress retention assembly in accordance with yet another embodiment of the present disclosure.

With reference to FIG. 23, another embodiment of a distal latch assembly configured to detachably support the buttress material 300 on the second jaw member 110 is generally shown as a distal latch assembly 1250. However, it is also contemplated that the distal latch assembly 1250 may be adapted for use with the first jaw member 108 including the staple cartridge 112. Parts of the distal latch assembly 1250 identical to those of the distal latch assembly 1150 will not be described to avoid obscuring the present disclosure in unnecessary detail.

The distal latch assembly 1250 includes a base 1220 configured to engage a distal end 110a (FIG. 22) of the anvil 111. The distal latch assembly 1250 includes a retention hook 1274 configured to be positioned in the knife slot 119 (FIG. 22) of the anvil 111 to urge the buttress material 300 inward towards the knife slot 119 when the buttress material 300 is disposed on the anvil 111. In particular, the retention hook 1274 includes a hook member 1275 dimensioned to be received in the knife slot 119 of the anvil 111, and a transverse member 1278 disposed orthogonal to the hook member 1275. Under such a configuration, in order to place the retention hook 1274 into the knife slot 119 of the anvil 111, the transverse member 1278 is first positioned in the knife slot 119 of the anvil 111 and the distal latch assembly 1250 is rotated about 90 degrees.

The base 1120 defines a slot 1224 dimensioned to receive at least a portion of the distal end 110a of the second jaw member 110 supporting the buttress material 300 thereon, and a lateral opening 1227 dimensioned to rotatably receive at least a portion of the distal end 110a of the second jaw member 110 therethrough. Under such a configuration, the buttress material 300 disposed on the anvil 111 may be secured to the base 1220 by rotatably placing the buttress material 300 and the anvil 111 into the slot 1224. The method of use of the distal latch assembly 1250 is substantially identical to those described hereinabove, and thus, will not be described.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling apparatus comprising:
    a handle including an actuation trigger;
    a tool assembly operatively coupled to the handle, the tool assembly including a first jaw member and a second jaw member; and
    a buttress retention assembly including:
        a sleeve configured to be detachably coupled with the first jaw member, the sleeve including proximal and distal portions, the proximal portion including a proximal hook extending transversely outward from at least one lateral side of the proximal portion, the distal portion including a mouth defining an aperture, the mouth including a hook configured to be at least partially received in a knife slot of the first jaw member, the mouth including an inner surface having an inwardly extending boss; and
        a buttress material including a proximal end portion and a distal end portion, the buttress material including a tab extending transversely outward from a lateral side of the proximal end portion, the tab defining a proximal slot configured to receive the proximal hook of the sleeve, at least a portion of the distal end portion extending through the aperture of the mouth of the sleeve, the distal end portion defining a distal slot dimensioned to receive the boss of the sleeve.

2. The surgical stapling apparatus according to claim 1, wherein the buttress material is formed of an elastic material such that when the buttress material is supported on the sleeve, cutting of the buttress material along a length thereof by a knife of the tool assembly causes the hook of the mouth to urge the buttress material inward towards the knife slot of the first jaw member, whereby the boss of the sleeve is released from the distal slot of the buttress material.

3. The surgical stapling apparatus according to claim 1, wherein the proximal end portion of the buttress material defines a slit dimensioned to receive a knife of the tool assembly.

4. The surgical stapling apparatus according to claim 1, wherein the sleeve includes an arcuate shape configured to receive the first jaw member.

5. The surgical stapling apparatus according to claim 1, wherein the proximal portion of the sleeve includes a plurality of lips extending transversely outward from opposing lateral sides thereof to engage the first jaw member.

6. The surgical stapling apparatus according to claim 5, wherein the proximal portion of the sleeve includes a plurality of proximal hooks disposed on the opposing lateral sides of the proximal portion of the sleeve.

7. The surgical stapling apparatus according to claim 5, wherein each proximal hook is interposed between adjacent lips.

8. The surgical stapling apparatus according to claim 1, wherein the sleeve is secured with the first jaw member by snap-fit or interference fit configuration.

9. The surgical stapling apparatus according to claim 1, wherein the mouth of the sleeve includes a nose having sides configured to displace the hook of the sleeve away from the first jaw member when the sides of the nose are squeezed together.

10. The surgical stapling apparatus according to claim 1, wherein the inner surface of the mouth defines an acute angle with respect to a longitudinal axis defined by the first jaw member.

11. A surgical stapling apparatus comprising:
    a tool assembly including first and second jaw members, the first jaw member defining a knife slot; and
    a buttress retention assembly including:
        a sleeve configured to be detachably coupled to the first jaw member, the sleeve including:
            a protuberance extending transversely outward from at least one lateral side of the sleeve; and a mouth defining an aperture, the mouth including a hook configured to be at least partially received in the knife slot of the first jaw member, the mouth including a boss; and a buttress material including a tab extending transversely outward from a lateral side thereof, the tab defining a first slot configured to receive the protuberance of the sleeve, at least a portion of the buttress material extending through the aperture of the mouth of the sleeve and defining a second slot dimensioned to receive the boss of the sleeve.

12. The surgical stapling apparatus according to claim 11, wherein the buttress material is formed of an elastic material such that when the buttress material is supported on the sleeve, cutting of the buttress material along a length thereof by a knife of the tool assembly causes the hook of the mouth to urge the buttress material inward towards the knife slot of the first jaw member, whereby the boss of the sleeve is released from the second slot of the buttress material.

13. The surgical stapling apparatus according to claim 11, wherein a proximal end portion of the buttress material defines a slit dimensioned to receive a knife of the tool assembly.

14. The surgical stapling apparatus according to claim 11, wherein a proximal portion of the sleeve includes a plurality of lips extending transversely outward from opposing lateral sides thereof to engage the first jaw member.

15. The surgical stapling apparatus according to claim 14, wherein the proximal portion of the sleeve includes a plurality of proximal hooks disposed on the opposing lateral sides of the proximal portion of the sleeve.

16. The surgical stapling apparatus according to claim 15, wherein each proximal hook of the plurality of proximal hooks is interposed between adjacent lips.

17. The surgical stapling apparatus according to claim 11, wherein the mouth includes an inner surface having the boss that extends inwardly from the inner surface.

* * * * *